US00PP25613P3

(12) United States Plant Patent
Egger

(10) Patent No.: US PP25,613 P3
(45) Date of Patent: Jun. 2, 2015

(54) ***AGASTACHE* PLANT NAMED 'KUDOS CORAL'**

(50) Latin Name: ***Agastache* hybrid**
Varietal Denomination: Kudos Coral

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 184 days.

(21) Appl. No.: 13/986,957

(22) Filed: Jun. 18, 2013

(65) Prior Publication Data

US 2014/0373235 P1 Dec. 18, 2014

(51) Int. Cl.
*A01H 5/02* (2006.01)

(52) U.S. Cl.
USPC ..... Plt./399

(58) Field of Classification Search
USPC ..... Plt./399
See application file for complete search history.

(56) References Cited

PUBLICATIONS

Internet Retrieval on http://www.greenhousegrower.com/varieties/terra-nova-nuseries for *agastache* cultivar named 'Kudo's Coral'. 2 pages total.*

* cited by examiner

*Primary Examiner* — Susan McCormick Ewoldt
(74) *Attorney, Agent, or Firm* — Klarquist Sparkman, LLP

(57) ABSTRACT

A new and distinct form of *Agastache* plant characterized by coral red flowers in large inflorescences, a long bloom time, a very short, compact habit, good winter hardiness, and excellent vigor.

1 Drawing Sheet

Botanical denomination: *Agastache* hybrid.
Variety designation: 'Kudos Coral'.

BACKGROUND OF THE INVENTION

The present invention relates to a new and distinct cultivar of *Agastache,* given the name, 'Kudos Coral'. *Agastache* is in the family Lamiaceae. This new variety is one of several selections of new *Agastache* using hardy and dwarf *Agastache* species in the breeding lines to provide hardiness and compactness. The new cultivar is a selection from the cross between the proprietary seedlings *Agastache* 46-1, as the seed parent, and *Agastache* 53-3, as the pollen parent. The new cultivar was selected for its compact habit, hardiness, and orange flowers in dense heads.

Compared to the seed parent, *Agastache* 46-1 the new cultivar is shorter and hardier with coral red flowers rather than orange.

Compared to the pollen parent, *Agastache* 53-3, the new cultivar is shorter and better branched.

Compared to *Agastache* 'Red Fortune', and unpatented plant, the new cultivar is much shorter.

This plant exhibits the following characteristics that make it unique:

1. coral red flowers on numerous inflorescences,
2. a long bloom time,
3. a very short, compact habit,
4. good winter hardiness,
5. and excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the new cultivar grown in a one gallon container in full sun in Canby, Oreg.

FIG. 2 shows nine-month-old *Agastache* 'Kudos Coral' growing in the field in mid summer in Canby, Oreg.

DETAILED PLANT DESCRIPTION

The following is a detailed description of the new *Agastache* cultivar based on observations of 4-month-old specimens in late May growing in full sun in a one gallon container in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, $5^{th}$ edition.

Plant:

*Form.*—Upright.
*Type.*—Herbaceous perennial.
*Cold hardiness.*—USDA Zone 6-10.
*Size.*—Grows to 28 cm wide and 35 cm tall to the top of the flowers.

*Vigor.*—Excellent.

*Branching.*—About 7 main stems from the base, these branch at every node.

*Stem.*—Square in cross section, grows to 4 mm wide and 28 cm tall to the first flower, pubescent, internodes range from 2 cm to 7 cm long, Yellow Green 147B.

*Roots.*—White 155B, fibrous, plants root easily from stem tip cuttings.

Leaf:

*Type.*—Simple.

*Arrangement.*—Opposite.

*Shape.*—Ovate.

*Venation.*—Pinnate.

*Margins.*—Crenate.

*Apex.*—Acute.

*Base.*—Truncate to cordate.

*Blade size.*—Grows to 30 mm long and 35 mm wide.

*Surface texture.*—Pubescent on both sides.

*Petiole description.*—Grows to 31 mm long and 1 mm wide, pubescent, Yellow Green 147B.

*Leaf color.*—Top side Yellow Green 147A including vein, bottom side closest to Yellow Green 147B with vein 147C.

*Fragrance.*—Aromatic.

Inflorescence:

*Type.*—Terminal spike with up to 9 whorls.

*Number of flowers.*—About 100 per spike.

*Size of inflorescence.*—Grows to 10 cm tall and 6 cm wide.

*Peduncle.*—Grows to 5 cm tall and 2 mm wide, pubescent, Yellow Green 147B.

*Pedicel.*—Grows to 2 mm long, pubescent, Greyed Purple N186C.

*Bloom period.*—June through frost in Canby, Oreg.

Flower bud:

*Size.*—27 mm long and 5 mm wide at the widest point prior to opening.

*Description.*—Tubular.

*Surface texture.*—Pubescent.

*Color.*—Red 47A.

Flower:

*Type.*—Zygomorphic.

*Shape.*—Bilabiate, tubular.

*Size.*—32 mm long and 7 mm wide.

*Corolla description.*—32 mm long and 7 mm wide; color both sides Red 47A; glabrous inside and pubescent outside, tube 27 mm long and 1 mm to 4 mm wide; 2 upper lobes joined 3 mm long and 4 mm wide, each oblong, tips obtuse, margin entire; three lower lobes, two spreading sideways and reflex, each 3 mm long and 2.5 mm wide, tip acute, margin entire; bottom lobe cupped, broadly obovate, notched at the tip, margin serrate, 6 mm wide and 4 mm deep.

*Calyx description.*—Campanulate, 7 mm long and 2 mm wide, pubescent outside and glabrous inside, 5 lobed, lobes ovate, 1.5 mm long, entire, acuminate, Greyed Purple N186C outside, inside Purple N77B.

*Pistil description.*—31 mm long, ovary 1 mm long, Yellow Green 145C, style 28 mm long, White NN155D at bottom blending to Purple Violet N81A at top, stigma two-parted, 1 mm deep, Purple N79C.

*Stamen description.*—4 in number, paired and exerted, top two 9 mm long and bottom two 7 mm long, filaments Red Purple 72C, anthers 1 mm long, Purple N77C, pollen White NN155D.

*Fragrance.*—Aromatic.

*Lastingness.*—A spike blooms for about 4 weeks on the plant.

Fruit/seed: 4 nutlets, 1 mm long, ovoid, Black 202A.

Pests and diseases: The new cultivar is typical to the genus. No known resistances to pests or diseases. No problems have been found in Canby, Oreg.

I claim:

1. A new and distinct form of *Agastache* plant substantially as shown and described.

* * * * *

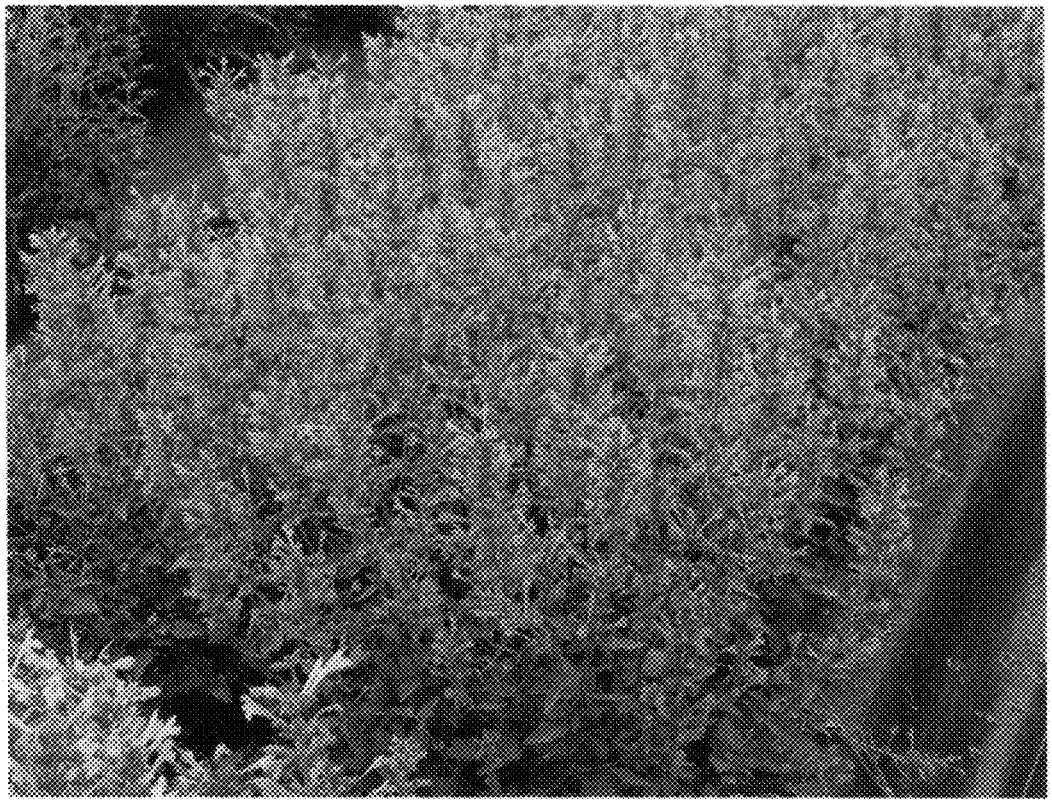

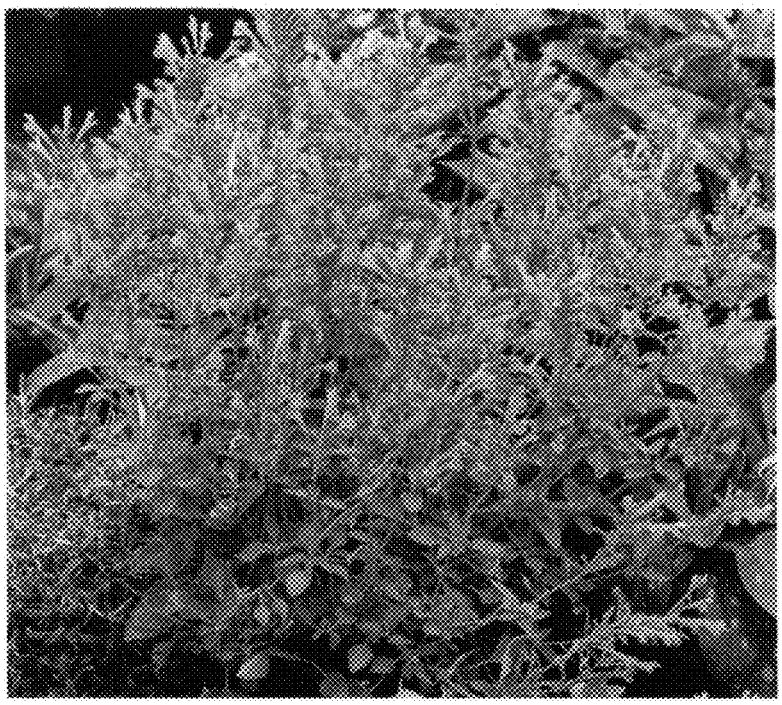
FIG. 1 above, FIG. 2 below